United States Patent

Robnett

[11] 4,229,164
[45] Oct. 21, 1980

[54] ORTHODONTIC METHOD AND MEANS

[76] Inventor: James H. Robnett, 4630-50th, Suite 505, Lubbock, Tex. 79414

[21] Appl. No.: 951,625

[22] Filed: Oct. 16, 1978

[51] Int. Cl.³ ............................................... A61C 7/00
[52] U.S. Cl. ..................................................... 433/20
[58] Field of Search ...................... 32/14; 433/20, 7, 6

[56] References Cited

U.S. PATENT DOCUMENTS 4,097,993  7/1978  Andrews .............................. 32/14 A Primary Examiner—Robert Peshock
Attorney, Agent, or Firm—Wendell Coffee

[57] ABSTRACT

A pattern for the construction of orthodontic appliances such as arch wires and retainers and positioners is made by three measurements of an individual's mouth: (1) the sum of the width of the mandibular six anterior teeth; (2) the width of the mandibular arch at the distal of the cuspids; and (3) the width of the arch at the mesio buccal cusp of the lower six year molars. The average measurement from the cuspid to the mesio buccal cusp of the mandibular six year molar is 18 mm and is used as a constant. From these measurements, a circular arc is formed between the cuspid width with the length of the arc equal to the sum of the width of the mandibular six anterior teeth. The pattern extends back for 18 mm between the cupsid width and the molar width and from there the line extends back at a angle. Since each of the measurements will vary, there will be a great but limited number of each measurement and, therefore, a limited combination of these measurements. Therefore, a series of patterns may be maintained so that the appliances may be shaped to this limited number of patterns.

8 Claims, 2 Drawing Figures

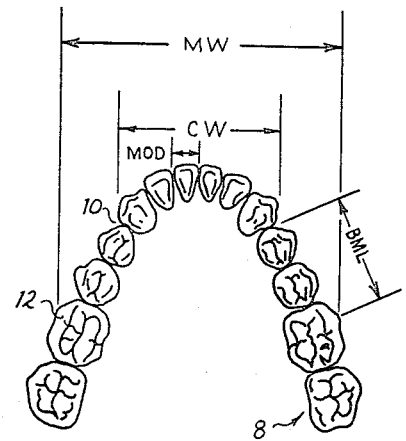
Fig. 1
Fig. 2
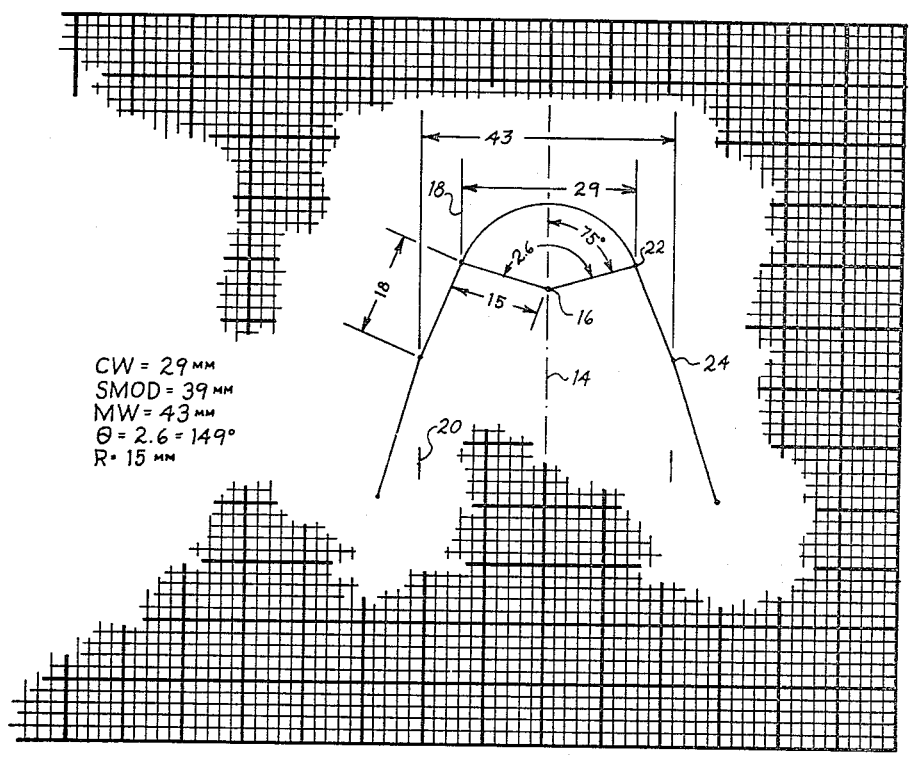

ORTHODONTIC METHOD AND MEANS

BACKGROUND OF THE INVENTION (1) Field of the Invention

This invention relates to orthodontic arch wires and retainers (32/14).

(2) Description of the Prior Art

As the term "appliances" is used throughout this paper, it is meant to include not only the metal arch wires but all appliances of similar nature made from other materials such as plastic, Fiberglas, alloys, synthetic resins, etc., and also other shapes rather than the traditional cross-section as well as devices to retain or position the teeth after they have been moved.

Use of appliances such as arch wires positioners and retainers in orthodontics is well known. This is shown among other things, by the establishment of a sub class in the U.S. Patent and Trademark Office, Class 32-Densitry, Sub Class 14A-Orthodontic Devices; Band Brackets and Arch Wires.

Details of the technique of bending the arch wire to an arch form is particularly set out by Strang in his textbook of Orthodontia (Lea & Febiger, 3rd Ed., Philadelphia 1950) particularly on pages 661–671. He also describes the method of drawing Bonwill-Hawley diagrams or arch forms on pages 658–661. Other standard curves, which are recognized as arch forms for arch wires, are:

1. the Parabola from Sicher, H.: Oral Anatomy; 5th Ed., St. Louis, 1970, The C. V. Mosby Co., P. 262;
2. the Ellipse from Brader, A. C.: American Journal of Orthodontics, Volume 61, Number 6, 1972, pages 541–561;
3. the Catenary from MacConnail, M. M.: The Ideal Form of the Human Dental Arcade, With Some Prosthetic Applications, Dent. Rec., 69: 285–302, 1949; and Scott, J. H.: The Shape of the Dental Arches, Jour. Dent. Res. 36: 996–1003, 1957; also
4. the Two Parameter Catenary (Rocky Mountain Data Systems, See Data-Bits, Profiles From RMDS, Number 10).

Positioners made of plastic or rubber material are on the market by at least two companies: OrthoTain and T. P. Laboratories.

Before this application was filed, a search was made in the U.S. Patent and Trademark Office and the following patents were reported on that search:

| | |
|---|---|
| 3,775,850 | Northcutt |
| 3,835,539 | Wallshein |
| 3,842,503 | Wildman |
| 3,879,849 | Schwartz |
| 3,906,634 | Aspel |
| 4,014,096 | Dellinger |

Applicant does not believe that these references are as pertinent as the publications specifically discussed above.

SUMMARY OF THE INVENTION (1) New and Different Function

I have a method whereby the arch patterns and, therefore, the appliances can be standardized for most individuals. Through experience I have found that my system will work on over 99% of the patients. The importance of this is that the appliances may be preformed commercially or fabricated by technicians, saving time formerly spent by the othodontist, according to three basic measurements. Therefore, the orthodontist is relieved of much of the time spent doing what can be done by a technician. Forming the appliances to my pattern has the benefit of having an appliance which is designed for the individual patient.

The pattern and the mandibular appliance is formed for the mandibular arch. The maxillary appliance is shaped to the mandibular pattern by gradual expansion in the cuspid and molar areas. The expansion is equal to the amount it is estimated the maxillary cuspids and molars are wider. The maxillary and mandibular appliances are formed on the basis:

(1) the six mandibular anterior teeth will be moved to a circular arc between the cuspids with correct anatomic positioning of the contact area;

(2) that the original cuspid width can be maintained;

(3) that the original molar width can be maintained;

(4) thus, the original shape of the arch can be maintained; and (5) controlled cuspid width and molar width changes can be made.

This concept is based on the assumption that the lower teeth in proper contact at proper incisal height (allowing proper interdigitation and occlusal contact) is circular in shape in the anterior area; then diverges bucco-laterally to the mesial-buccal cusp of the first molar and then at about 15° disto lingually.

Therefore, the arch pattern is not necessarily a representation of the so called "normal arch form" but is a design from which orthodontic appliances can be constructed within precise mathmatical limits so that the teeth can be properly aligned within the anatomical boney arches. My pattern will demonstrate where expansion or constriction of the cuspids will occur to accomodate the unpredictable arch length formed by the width of the six lower anterior teeth. The pattern can be described as a representation of the "line of occulsion" adjusted to allow correct alignment of the teeth according to their individual buccal-lingual thickness.

Further, I have observed that if all measurements are made to within 1 mm, they are sufficiently accurate for all orthodontic purposes.

Thus, it may be seen that the sum of the total function of my invention is far greater than the sum of the functions of the individual parts.

OBJECTS OF THIS INVENTION

An object of this invention is to properly align teeth within the anatomical boney arches for pleasing appearance and proper functioning, more efficiently and with greater stability.

Further objects are to achieve the above with a device that is sturdy, compact, durable, lightweight, simple, safe, efficient, versatile, ecologically compatible, energy conserving, and reliable, yet inexpensive and easy to manufacture, install, adjust, and maintain.

Other objects are to achieve the above with a method that is versatile, ecologically compatible, energy conserving, rapid, efficient, and inexpensive, and allows any bends or any arch wires to be consistent in size and shape, in sequence, throughout treatment.

The specific nature of the invention, as well as other objects, uses, and advantages thereof, will clearly appear from the following description and from the accompanying drawing.

BRIEF DESCRIPTION OF THE DRAWINGS

FIG. 1 is a top plan view of a mandibular arch model.

FIG. 2 is a pattern according to my invention drawn on graph paper, with the graph lines not shown in the area of the arch pattern for clarity.

DESCRIPTION OF THE PREFERRED EMBODIMENTS

To properly practice my invention, the first step is to make maxillary and mandibular models of the arches to be corrected. From the mandibular arch 8 (FIG. 1) certain measurements are taken. First, the cuspid width (CW) is determined. This width is measured at the distal 10 of the cuspids. A certain amount of artistic and mechanical interpretation is necessary in determining the CW.

The second step is to measure the mesio-distal diameter (MOD) of each of the six anterior teeth. These six MOD's are added together to obtain the sum of the mesio-distal diameters (SMOD).

Third, the molar width (MW) is determined by measuring the width of the arch at the mesial-buccal cusp 12 of the first molar, sometimes called the six year molar.

I have found patterns may be made and appliances formed with sufficient accuracy if it is assumed that the bi-molar length (BML) is 18 mm. I.e., the distance from the distal of the cuspids to the mesial-buccal cusp of the first molar on the mandibular model will be about 18 mm. If it is more or less than 18 mm, it is of no real significance because there is very slight change in the form of the wiring in this area. Also, the practice of extracting bicuspids automatically requires moving this point mesially along this line.

From the SMOD and the CW, the radius (R) of the circular arc for the six anterior teeth is determined. Also, the included angle in radians ($\theta$) of the length of this arc is determined. This is determined from the two basic formulas:

$$R = \frac{SMOD}{\theta} = \frac{\frac{1}{2} CW}{\sin \frac{1}{2} \theta}$$

I have found from a large number of patients which have consulted me that the CW will be within a range of 25 mm to 36 mm and that 98% will be within the range of 27 mm to 34 mm.

Also, I have determined that the SMOD will range between 33 mm and 44 mm with 98% being between 35 mm and 42 mm. After determining on the basis of the two formulas above the radius for a large number of patients, I find the radius will range from about 13 mm to about 24 mm. The included angles will range from about 85° to nearly a full semi-circle or about 175°. There will be about 100 combinations of measurements for the six anterior teeth if they are taken on a 1 mm gradient of the CW and SMOD. I.e., from a large number of patients that I have studied, that they would all fall within 1 mm of the CW and SMOD measurements of 100 possible combinations.

With the inclusion of the molar width, I have found that about 600 combinations will exist for all normal patients.

Further anaylsis will show that as the angle theta reaches a point of about 2.4 radians or about 135° that the radius R for the circular arc changes very slightly. Also, at this value of theta, experience will show that the molar line will be about tangent to the circular arc. Therefore, for all practical purposes, a pattern or chart is sufficient for all practical purposes of use by the orthodontist if the radius is within 0.2 mm of a calculated amount. Therefore, as a practical matter, I have found that working charts having only 58 different combinations of the circular arcs for the six anterior teeth are necessary and that only 348 charts or working patterns are necessary. Although this is a large number of patterns, it will be understood that there is a great advantage if the three measurements, i.e., the SMOD, CW and MW can be provided for a patient and from a fixed number or limited number of charts, i.e., 348 charts, the arch wire can be formed according to a predetermined or preexisting pattern. Since 95% of the orders for arch wires will be from a limited number of patterns, it is possible that the arch wires for the more common sizes could be maintained in stock. Those for the less common size could be quickly formed from a pre-existing pattern. A far lesser number of retainers and positioners will be required.

To draw the pattern from the measurements, first it is most convenient to draw on grid paper 2 mm × 2 mm, FIG. 2. A line is designated as the axis 14 of the arch and an arc is struck with the center 16 of the arc on the axis and the arc extending with a chord equal to the CW.

CW lines 18 are drawn by drawing the lines parallel to the axis line one-half the CW measurement from the axis (or designating a grid line as the CW line). On the example shown in FIG. 1, the CW is measured as 29 mm. Therefore, the CW lines 18 would be constructed 14½ mm from the axis 14 and parallel thereto. Also as it may be seen from the model shown in FIG. 1, the SMOD is determined to be 39 mm and, therefore, according to the formula above the radius will be 15 mm and the included angle theta will be equal to 2.6 radian or 149°. Half theta, therefore, will be equal to about 75°. The molar width of the model, shown in FIG. 1, is determined to be about 43 mm and then the molar width lines 20 are drawn by again taking half the molar width or 21½ mm and drawing them parallel to the axis 14 (or designating a grid line as the MW line). As stated before, the bi-molar length is assumed to be 18 mm. Therefore, from the point 22 where the arc, struck from center 16, intersects the CW line 18, a bi-molar line (BML) is drawn for 18 mm to point 24 where it intersects the MW line 20. This is done most conveniently by setting a compass with 18 mm between the points and setting one point at the point 22 and thereby determining where the point 24 would fall upon the MW line 20. From this point, the molar line is drawn at an angle.

Therefore, it may be seen that it is a simple matter for a technician to draw the 348 working patterns that would evolve from the possible combinations having a cuspid width from 25 mm to 36 mm and an SMOD between 33 mm and 44 mm when in no case will the included angle be less than 85° or more than 175° and the radius being no less than 13 mm nor greater than 24 mm. I found that the molar width of all patients I have checked will be within a limited range.

Therefore, it may be seen that 348 working charts or patterns may be prepared that would match practically all of the mandibular arches that occur naturally. Then arch wires may be prepared for the 288 or so that would occur in 95% of all patients. Therefore, when an orthodontist begins treatment, all that would be necessary is for him to make the three measurements, CW, MW and SMOD and to thereby obtain preformed arch wires from existing stock in 95% of the cases.

Therefore, it may be seen that this would greatly simplify and expedite the work of the orthodontist.

The embodiment shown and described above is only exemplary. I do not claim to have invented all the parts, elements or steps described. Various modifications can be made in the construction, material, arrangement, and operation, and still be within the scope of my invention. The limits of the invention and the bounds of the patent protection are measured by and defined in the following claims. The restrictive description and drawing of the specific example above do not point out what an infringement of this patent would be, but are to enable the reader to make and use the invention.

I claim as my invention:

1. The method of forming the curvature of orthodontic appliances such as arch wires, retainers and positioners wherein the appliance requires an arch shaped portion comprising the steps of:
    a. determining the
        (i) sum of the mesio-distal diameters of the six anterior teeth,
        (ii) cuspid width, and
        (iii) molar width of the mandibular arch, then
    b. drawing a pattern by
    c. drawing an axis line,
    d. drawing two cuspid width lines each parallel to the axis and spaced one-half the determined cuspid width from the axis,
    e. drawing two molar width lines each parallel to the axis and spaced one-half the determined molar width from the axis,
    f. striking a circular arc with the center on the axis and arc length between the cuspid width lines equal to the determined sum of the mesio-distal diameters, and thereafter
    g. extending a bi-molar line from each intersection of the arc and the cuspid width line to the molar width line, and
    h. forming the arch shaped portion of the appliance to said pattern.

2. The invention as defined in claim 1 further comprising:
    j. striking the arc by determining the radius of the arc to meet the limitations that an arc length equal to the sum of the mesio-distal diameters has a chord equal to the cuspid width.

3. The invention as defined in claim 1 further comprising:
    j. extending said bi-molar line for 18 mm, and thereafter
    k. extending an angled molar line.

4. The invention as defined in claim 3 further comprising:
    m. striking the arc by determining the radius of the arc to meet the limitations of an arc length equal to sum of the mesio-distal diameters is equal to the cuspid width.

5. An appliance having an arch shaped portion such as arch wires, retainers and positioners for a mandibular and a maxillary arch having a certain mandibular
    (i) sum of the mesio-distal diameters of the six anterior teeth,
    (ii) cuspid width, and
    (iii) molar width
comprising:
    a. the arch shaped portion of said appliance constructed to correspond to a pattern,
    b. said pattern having an axis,
    c. a front circular arc having
        (i) a chord equal to the cuspid width,
        (ii) an arch length equal to the sum of the mesio-distal diameters, and
        (iii) its center on the axis,
    d. a straight bi-molar line extending from each end of the arc.

6. The invention as defined in claim 5 further comprising:
    e. said bi-molar line extending for 18 mm and the distal ends of the bi-molar line being at a distance from each other equal to the molar width,
    f. a straight molar line extending from each end of the bi-molar line at an angle.

7. The method of forming the curvature of orthodontic applicances such as arch wires, retainers and positioners wherein the appliance requires an arch shaped portion for mandibular and maxillary arches comprising the steps of:
    a. measuring at least three dimensions of the mandibular arch, and
    b. forming the arch shaped portion of the appliance to correlate to said measurements.

8. The invention as defined in claim 7 wherein
    c. the three measured dimensions are the cuspid width, the molar width and the sum of the mesio-distal diameters of the six anterior teeth of the mandibular arch.

* * * * *